(12) United States Patent
Naik et al.

(10) Patent No.: US 10,818,008 B2
(45) Date of Patent: Oct. 27, 2020

(54) METHOD AND SYSTEM FOR DETERMINING RADIOPHARMACEUTICAL COMPOUNDS USED IN MEDICAL IMAGING

(71) Applicants: Sandesh Naik, Uttara Kannada (IN); Arunabha Roy, Navi Mumbai (IN)

(72) Inventors: Sandesh Naik, Uttara Kannada (IN); Arunabha Roy, Navi Mumbai (IN)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 95 days.

(21) Appl. No.: 16/011,101

(22) Filed: Jun. 18, 2018

(65) Prior Publication Data
US 2019/0385304 A1 Dec. 19, 2019

(51) Int. Cl.
| | | |
|---|---|---|
| *G16C 20/40* | (2019.01) | |
| *G06K 9/44* | (2006.01) | |
| *G06T 7/10* | (2017.01) | |
| *G06T 7/00* | (2017.01) | |
| *G06K 9/32* | (2006.01) | |
| *G06K 9/42* | (2006.01) | |
| *G16C 20/20* | (2019.01) | |

(52) U.S. Cl.
CPC .......... *G06T 7/0012* (2013.01); *G06K 9/3233* (2013.01); *G06K 9/42* (2013.01); *G16C 20/20* (2019.02); *G06K 2209/05* (2013.01); *G06T 2207/10104* (2013.01); *G06T 2207/10108* (2013.01)

(58) Field of Classification Search
USPC ......... 382/128–134, 154, 162–230, 254–309
See application file for complete search history.

(56) References Cited

U.S. PATENT DOCUMENTS

| | | | | |
|---|---|---|---|---|
| 2010/0145194 A1* | 6/2010 | Joshi | ......................... | A61B 6/00 600/431 |
| 2016/0070007 A1* | 3/2016 | Vetter | .................... | G01T 1/2964 250/395 |
| 2019/0021608 A1* | 1/2019 | Cope | ..................... | A61K 51/025 |

OTHER PUBLICATIONS

Gray, Katherine Rachel. "Machine learning for image-based classification of Alzheimer's disease." Diss. Imperial College London, Oct. 2012. pp. 1-205.

* cited by examiner

*Primary Examiner* — Marcellus J Augustin
(74) *Attorney, Agent, or Firm* — Lempia Summerfield Katz LLC

(57) ABSTRACT

A method and system for determining a radiopharmaceutical compound in a medical image is disclosed. In one embodiment, the method includes obtaining the medical image from a medical imaging device through an interface. The method also includes identifying a region of interest in the medical image. The method further includes generating a feature vector associable with the region of interest. Additionally, the method includes detecting an uptake of the radiopharmaceutical compound in the region of interest. Furthermore, the method includes identifying a type of the radiopharmaceutical compound in the region of interest based on the feature vector and a biological information associated with the region of interest.

17 Claims, 10 Drawing Sheets

FIGURE 7
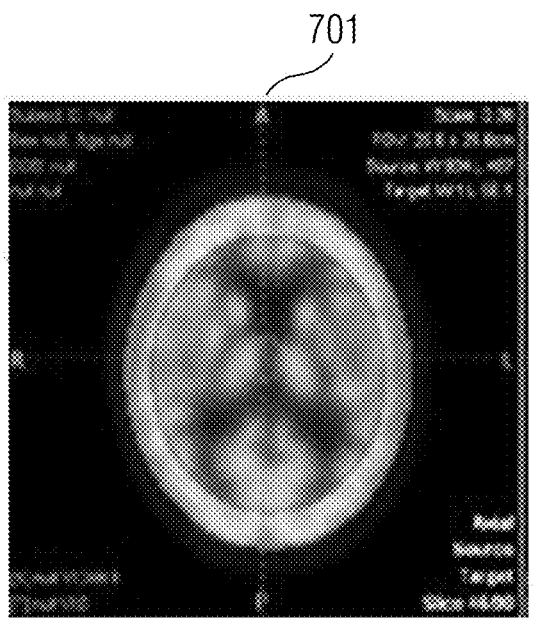
701
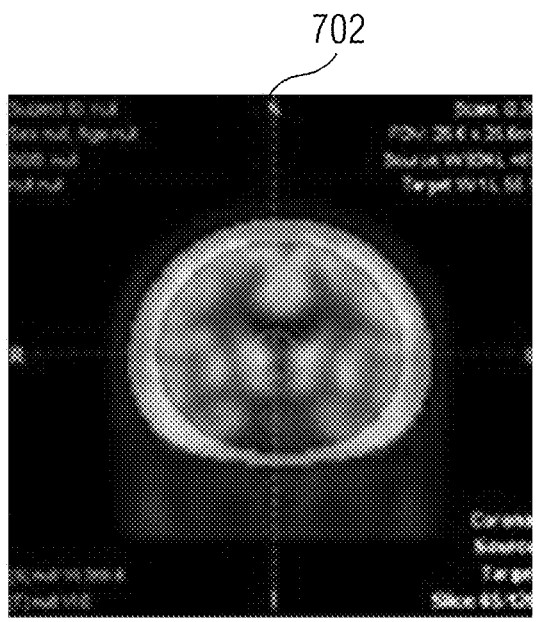
702
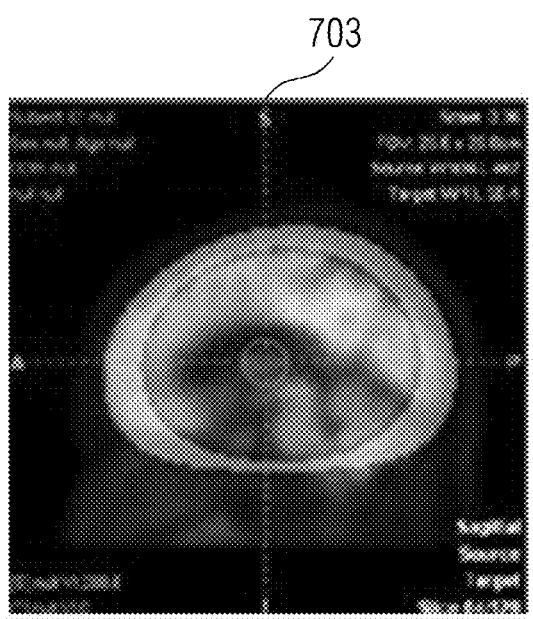
703

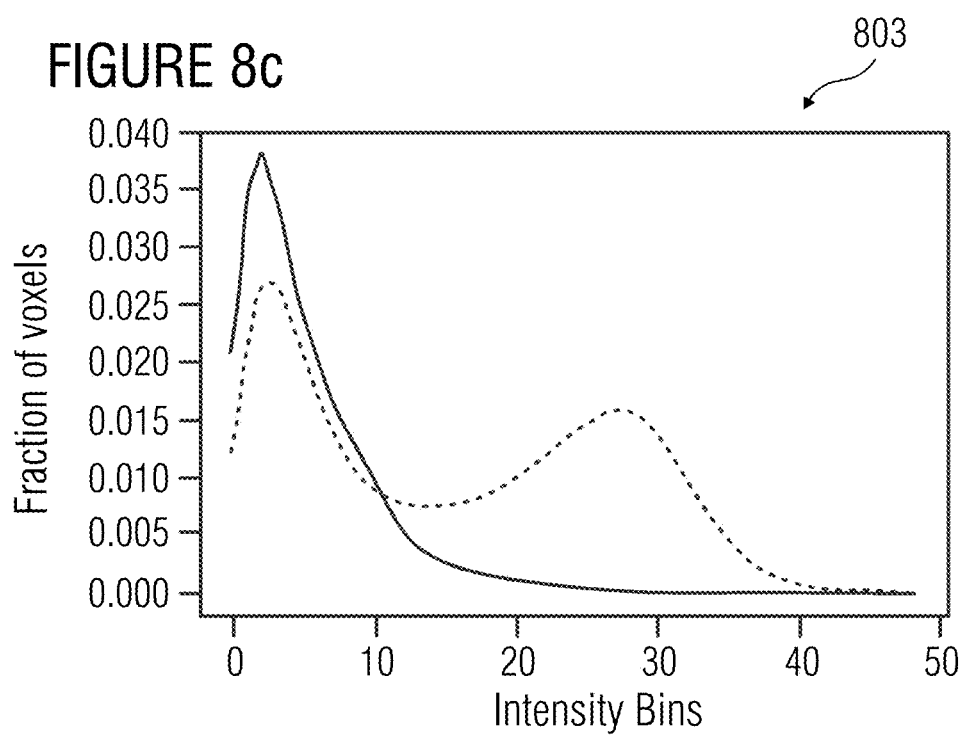

METHOD AND SYSTEM FOR DETERMINING RADIOPHARMACEUTICAL COMPOUNDS USED IN MEDICAL IMAGING

FIELD OF TECHNOLOGY

The present disclosure relates to the field of analysis of medical images and more particularly to the field of determining radiopharmaceutical compounds in medical images.

BACKGROUND

Nuclear medicine imaging techniques such as positron emission tomography (PET) and single-photon emission computed tomography (SPECT) involve delivery of a radioisotope into a patient to be examined. Such radioisotopes are capable of emitting gamma radiation and are known as radiopharmaceutical compounds or radiotracers. Several radiopharmaceutical compounds are used today in medical imaging. The knowledge of the radiopharmaceutical compound used in an imaging process enables a user, for example a physician, to perform a variety of complex image processing, statistical and alternative numerical evaluations pertaining to the scan which may enrich diagnosis. For example, a patient's medical image may be compared with an atlas of standardized patients specific to the radiopharmaceutical compound in order to gauge medical abnormalities. In molecular imaging medical images, a Digital Imaging and Communications in Medicine (DICOM) header may contain information about the radiopharmaceutical compound used in image acquisition. However, such information about the radiopharmaceutical compound is populated manually by a technologist operating the imaging system. Therefore, such information may be unreliable, missing or lacking standardization. Therefore, such information cannot always be used with confidence. Therefore, there is a need for a method to determine the radiopharmaceutical compound accurately and reliably to enhance image analysis workflows.

The object of the disclosure is therefore to provide a method and a system to determine a radiopharmaceutical compound from a medical image that is accurate and reliable.

SUMMARY

A method and system for determining a radiopharmaceutical compound in a medical image are disclosed. In one aspect, the method includes obtaining the medical image from a source through an interface. The method also includes identifying a region of interest in the medical image. Additionally, the method includes generating a feature vector associable with the region of interest. Furthermore, the method includes detecting the uptake of the radiopharmaceutical compound in the region of interest. The method also includes identifying a type of the radiopharmaceutical compound in the region of interest based on the feature vector and a location of the region of interest.

In another aspect, a system for determining a radiopharmaceutical compound in a medical image includes a processing unit, a medical database coupled to the processing unit, and a memory coupled to the processing unit. The memory includes an identification module configured for obtaining the medical image from a source, through an interface. The identification module is further configured for identifying a region of interest in the medical image. Furthermore, the identification module is configured for generating a feature vector associable with the region of interest. Additionally, the identification module is configured for detecting the radiopharmaceutical compound in the region of interest. The identification module is also configured for identifying a type of the radiopharmaceutical compound in the region of interest based on the feature vector and a location of the region of interest.

In yet another aspect, a non-transitory computer-readable storage medium having machine-readable instructions stored therein, that when executed by the server, causes the server to perform the method acts as described above.

This summary is provided to introduce a selection of concepts in a simplified form that are further described below in the following description. It is not intended to identify features or essential features of the claimed subject matter. Furthermore, the claimed subject matter is not limited to implementations that solve any or all disadvantages noted in any part of this disclosure.

BRIEF DESCRIPTION OF THE DRAWINGS

The present disclosure is further described hereinafter with reference to illustrated embodiments shown in the accompanying drawings, in which:

FIG. 7 illustrates an embodiment of a set of medical images depicting the cortical region of a brain in a PET scan in three orthogonal views.

FIG. 8c illustrates an embodiment of an averaged feature vector of two radiopharmaceutical compounds.

DETAILED DESCRIPTION

Figure 1:
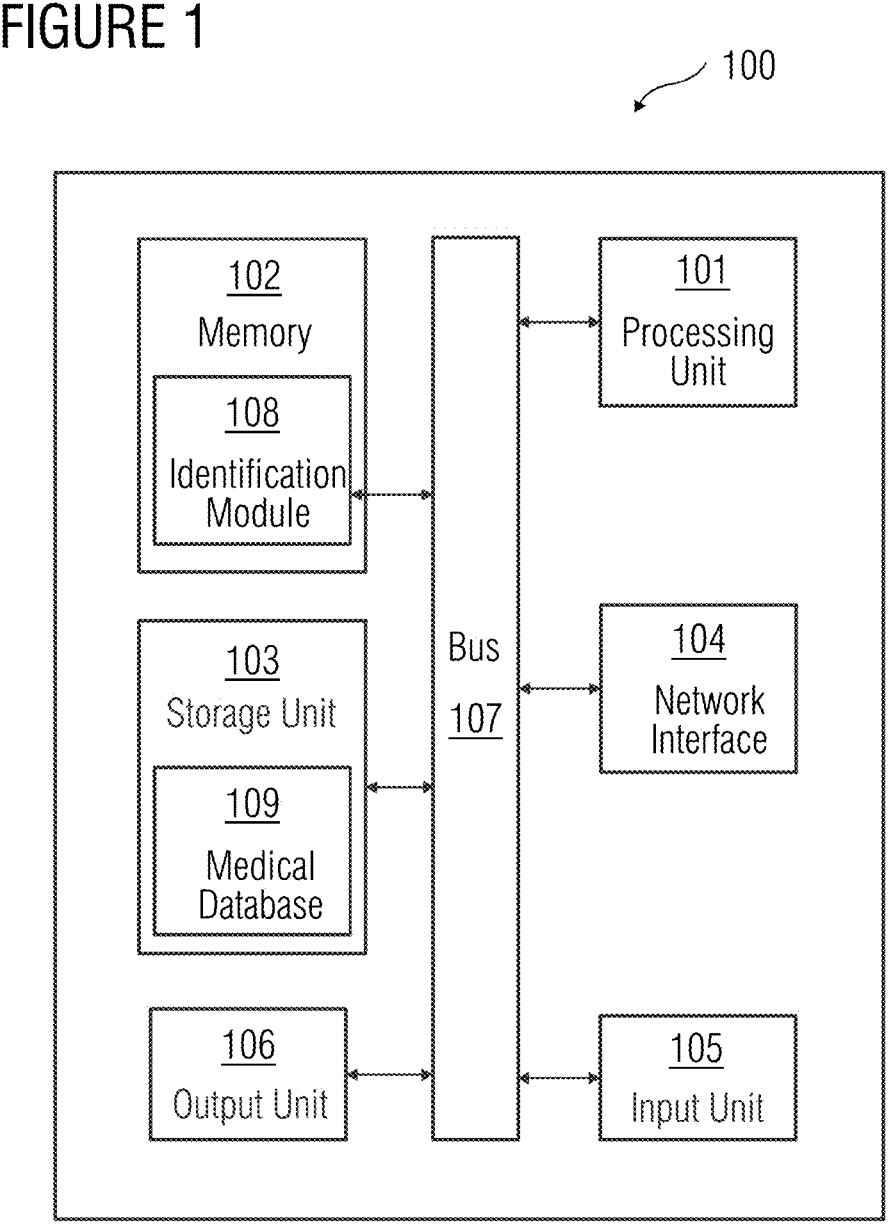
FIG. 1 illustrates a block diagram of a system in which an embodiment of a method for determining a radiopharmaceutical compound from a medical image may be implemented.

Hereinafter, embodiments for carrying out the present disclosure are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details. In other instances, well known materials or methods have not been described in detail in order to avoid unnecessarily obscuring embodiments of the present disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the present disclosure.

FIG. 1 is a block diagram of a system 100 in which an embodiment may be implemented, for example, as a system to determine a radiopharmaceutical compound in a medical image, configured to perform the processes as described therein. In FIG. 1, the system 100 includes a processing unit 101, a memory 102, a storage unit 103, a network interface 104, an input unit 105, an output unit 106 and a standard interface or bus 107. The system 100 may be a (personal) computer, a workstation, a virtual machine running on host hardware, a microcontroller, or an integrated circuit. As an alternative, the system 100 may be a real or a virtual group of computers (the technical term for a real group of computers is "cluster", the technical term for a virtual group of computers is "cloud").

The processing unit 101, as used herein, refers to any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processing unit 101 may also include embedded controllers, such as generic or programmable logic devices or arrays, application specific integrated circuits, single-chip computers, and the like. In general, a processing unit 101 may include hardware elements and software elements. The processing unit 101 may be configured for multithreading, (e.g., the processing unit 101 may host different calculation processes at the same time), executing the either in parallel or switching between active and passive calculation processes.

The memory 102 may be volatile memory and non-volatile memory. The memory 102 may be coupled for communication with the processing unit 101. The processing unit 101 may execute instructions and/or code stored in the memory 102. A variety of computer-readable storage media may be stored in and accessed from the memory 102. The memory 102 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In one embodiment, the memory 102 includes an identification module 108 stored in the form of machine-readable instructions on any of the above-mentioned storage media and may be in communication to and executed by processing unit 101. When executed by the processing unit 101, the identification module 108 causes the processing unit 101 to determine a radiopharmaceutical compound from the medical image. Method acts executed by the processing unit 101 to achieve the abovementioned functionality are elaborated upon in detail in FIGS. 2, 3, 4, 5, 7, 8a, 8b, 8c, and 9.

The storage unit 103 may be a non-transitory storage medium which stores a medical database 109. The medical database 109 is a repository of medical information related to one or more patients that is maintained by a healthcare service provider. The input unit 105 may include an input device such as keypad, touch-sensitive display, camera (such as a camera receiving gesture-based inputs), etc. capable of receiving input signal. The bus 107 acts as interconnect between the processing unit 101, the memory 102, the storage unit 103, the network interface 104, the input unit 105, and the output unit 106.

Those of ordinary skilled in the art will appreciate that the hardware depicted in FIG. 1 may vary for particular implementations. For example, other peripheral devices such as an optical disk drive and the like, Local Area Network (LAN)/Wide Area Network (WAN)/Wireless (e.g., Wi-Fi) adapter, graphics adapter, disk controller, or input/output (I/O) adapter also may be used in addition or in place of the hardware depicted. The depicted example is provided for the purpose of explanation only and is not meant to imply architectural limitations with respect to the present disclosure.

A system in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through the pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Wash. may be employed if suitably modified. The operating system is modified or created in accordance with the present disclosure as described.

Disclosed embodiments provide systems and methods for analysing a medical image. In particular, the systems and methods may determine a radiopharmaceutical compound in a medical image.

Figure 2:
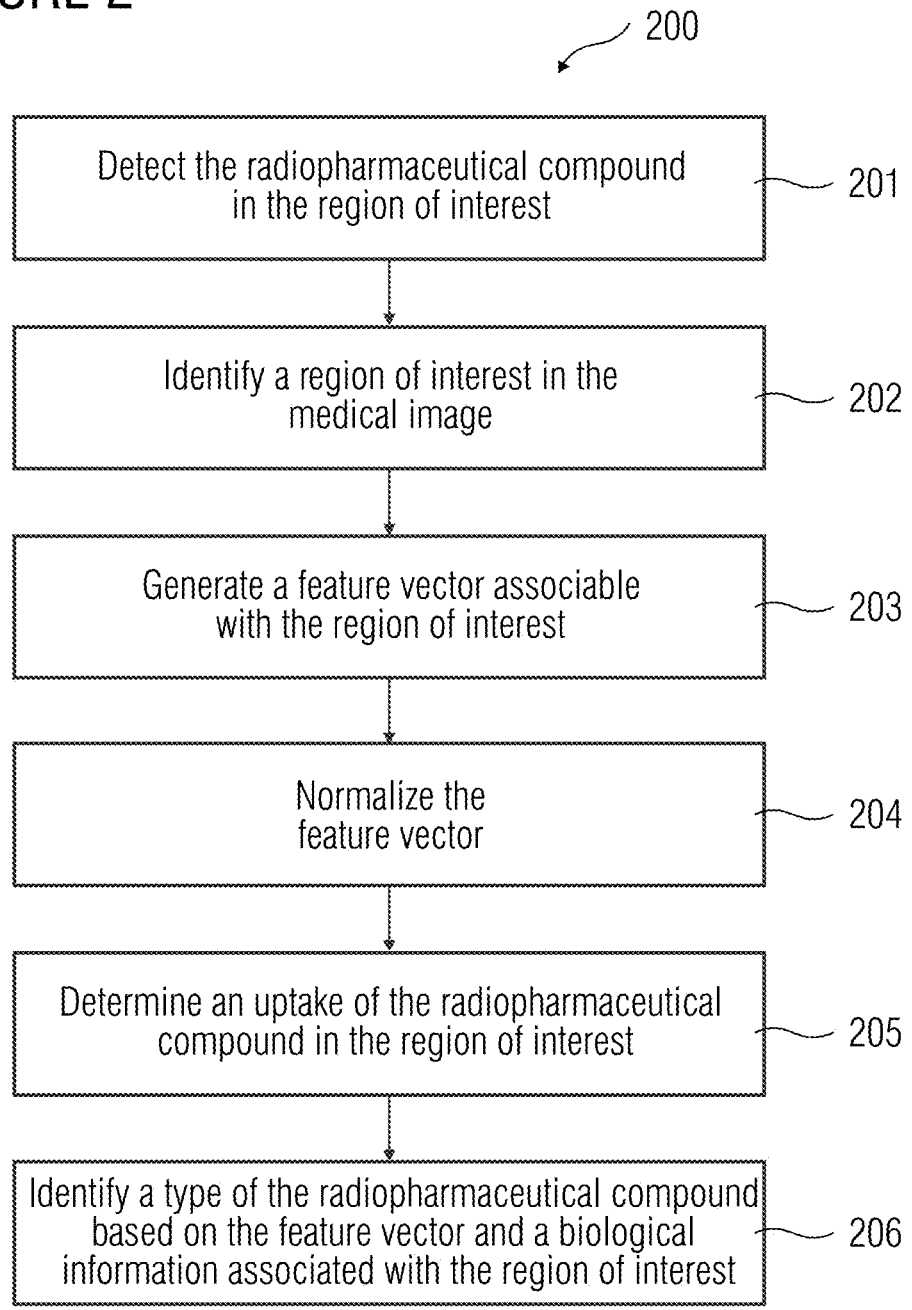
FIG. 2 illustrates a flowchart of an embodiment of a method of determining a radiopharmaceutical compound from a medical image.
Figure 6:
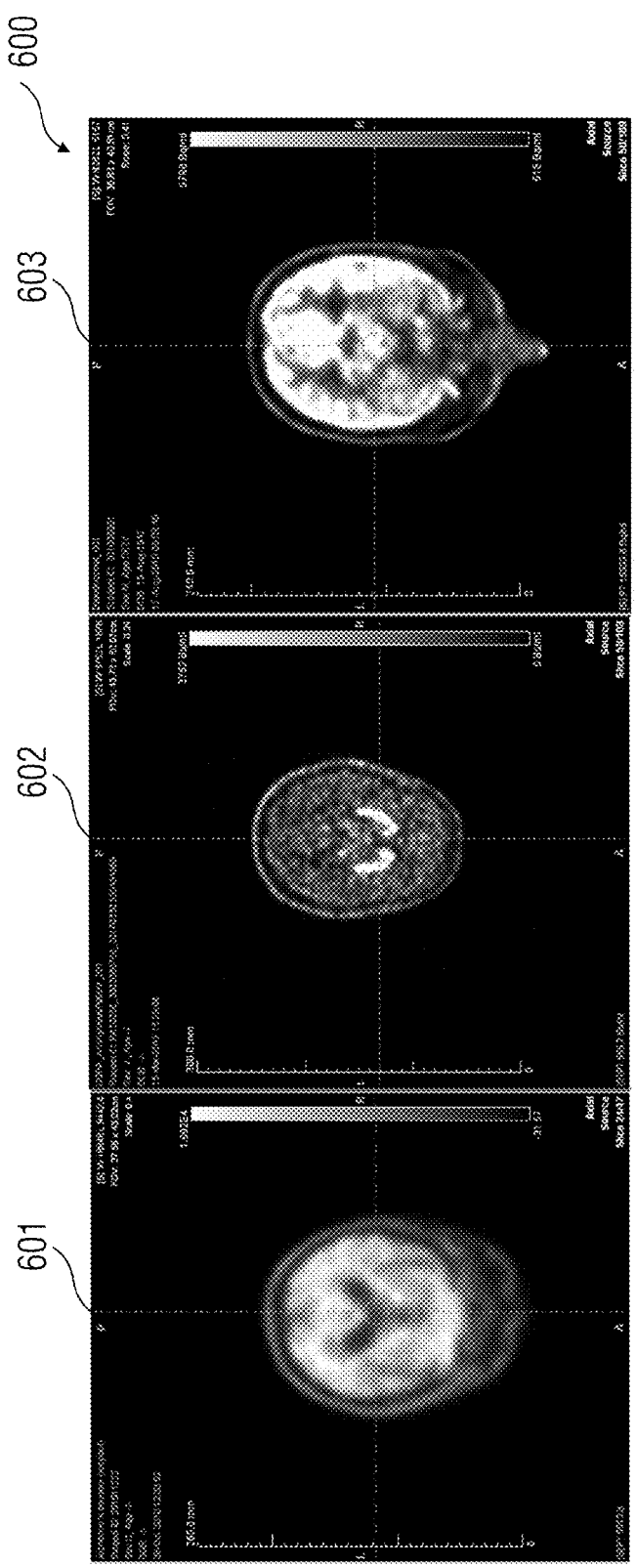
FIG. 6 illustrates an embodiment of a set of medical images of an anatomical region depicting the uptake of a plurality of radiopharmaceutical compounds.

FIG. 2 illustrates a flowchart of an embodiment of a method 200 of determining the radiopharmaceutical compound used in the medical image. At act 201, the medical image is obtained from a source, through an interface. The source may be, for example, a medical imaging device. The interface may a standard interface 107 or a network interface 104. The medical imaging device may be, for example, a positron emission tomography (PET) scanner or a Single-Photon Emission Computed Tomography (SPECT) scanner. Therefore, the medical image may be for example, a PET image, or a SPECT image. PET or SPECT imaging enables monitoring of biological or metabolic activity in a body of a patient. PET and SPECT imaging involves use of radiopharmaceutical compounds to observe such biological or metabolic activities in the body. The radiopharmaceutical compound is a biological molecule associated with a specific metabolic function of the human body, in which one of the atoms is a radioactive isotope that acts as a positron (e.g., in PET imaging) or gamma (e.g., in SPECT imaging) emitter. Therefore, radiopharmaceutical compounds may be chosen based on the type of biological molecule or the location to be monitored. For example, FIG. 6 illustrates an embodiment of a set 600 of medical images 601, 602, 603 depicting axial slices of a brain with different radiopharmaceutical compounds. Based on the type of the radiopharmaceutical compound used for imaging, a different location in the brain is enhanced. The distribution of the radiopharmaceutical compound in the medical image may indicate the concentration of the corresponding biological molecule present in the imaged part of the body. This may enable determination of tissue metabolic activity. For example, if the radiopharmaceutical compound used for PET imaging is fluorodeoxyglucose (FDG), an analogue of glucose, the concentration of the radiopharmaceutical compound in the body indicates the tissue metabolic activity, as it corresponds to regional glucose uptake. In an embodiment, the medical image may be obtained by the system from the medical imaging device through a network interface 104. Alternatively, the medical image may also be obtained from the medical database 109. The medical database 109 may contain all the images acquired by the medical imaging device.

Figure 3:
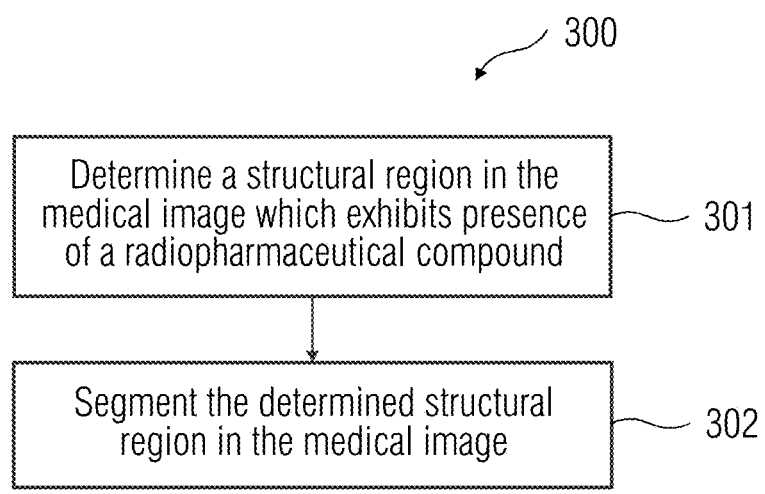
FIG. 3 illustrates a flowchart of an embodiment of a method of identifying a region of interest in a medical image.

At act 202 of the method 200, one or more regions of interest are identified in the medical image. The radiopharmaceutical compound is capable of emitting gamma rays, which are detected by the medical imaging device during the image acquisition process. The medical image may contain certain regions indicating high activity concentration (e.g., intensity of the image). Such regions may appear enhanced over other regions in the medical image. FIG. 3 illustrates an embodiment of a method 300 of identifying the region of interest in the medical image. At act 301, the structural region in the medical image exhibiting presence of the radiopharmaceutical compound is determined. The medical image may be processed to identify the region based on pixel values associated with the medical image. The region of interest may also be identified from the medical image geometrically. In an alternate embodiment, the medical image may be registered to a labelled structural image to determine the mapping region of interest in the medical image. For example, a computed tomography image or a magnetic resonance imaging image of the same patient, in which the region of interest may be readily identifiable, may be used via multi-modality image registration to identify the region of interest in the medical image. In yet another embodiment, a radiopharmaceutical compound-agnostic atlas may be used to identify the region of interest in the medical image. In an alternate embodiment, at act 302 of the method 300, the determined region of interest may be segmented from the medical image. The segmentation of the region of interest may be performed using one or more automated segmentation algorithms that may be known to a person skilled in the art. FIG. 7 illustrates an embodiment of a set of medical images 701, 702, 703 depicting the cortical region of the brain. The cortical region in the images 701, 702, and 703 is enhanced due to the presence of radiopharmaceutical compounds. In an embodiment, such cortical region in the image may be segmented out for generation of a feature vector.

At act 203 of the method 200, a feature vector associable with the one or more regions of interest, is generated. A feature vector is a vector which contains information describing the characteristics of the medical image. In an embodiment, the feature vector may be, for example, a histogram of the medical image. The histogram may be calculated for a set of intensity values of the pixels in the region of interest. For example, the histogram may be plotted for the cortical region of the brain depicted in FIG. 7. The histogram of uptake of the radiopharmaceutical compound in the cortex region is known to be a differentiator between amyloid and FDG tracers. Therefore, the cortex region may be chosen as the region of interest. The X-axis of the histogram indicates intensity bins and the Y-axis of the histogram indicates fraction of voxels in the region of interest. A desirable requirement of the features in the feature vector is independence of spatial scale and intensity. Spatial scale-independence of spatial features, for example, mandates that the length of the imaged object not be defined in pixel or mm units but be, for example, normalized to some reference organ length for the patient. Therefore, medical images obtained at varying pixel resolution for patients of variable anatomical sizes may not produce features of varying magnitude for what is the same underlying extent of the image object. Similarly, intensity normalization may also be crucial as the number of counts obtained in a PET image is directly proportional to an injected dose of the radiopharmaceutical compound. The amount of dose of the radiopharmaceutical compound varies as per imaging protocols adopted by different institutions. For example, the amount of dose may be as much as 50% different at a single site of imaging. Therefore, the implications of the dose on the image intensity derived features may be immediate, e.g., a feature defined using intensity alone may vary by 50% for features that are linear in intensity, and by even a larger and unpredictable amount for non-linear features. Therefore, normalization of the features based on scale and intensity is needed. At act 204 of the method 200, the feature vector is normalized to be spatial-scale and/or intensity-independent.

Figure 5:
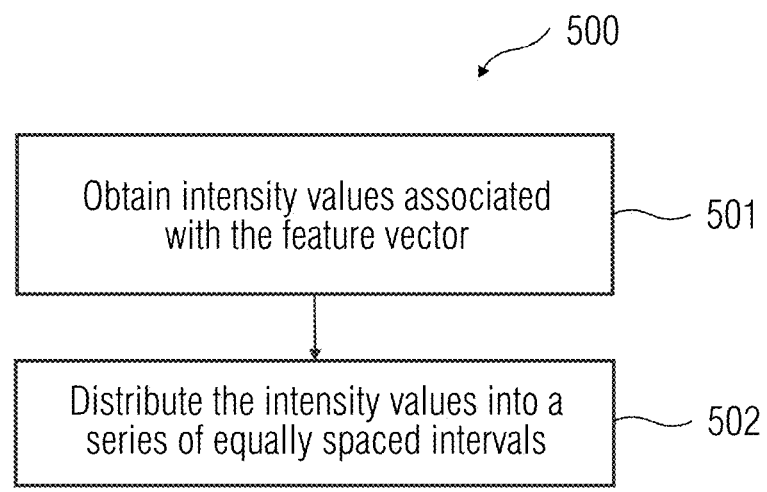
FIG. 5 illustrates a flowchart of an embodiment of a method of normalizing a feature vector.

FIG. 5 illustrates a flowchart of an embodiment of a method 500 of normalizing the feature vectors to be intensity-independent. In the embodiment, the feature vector to be normalized may be a histogram. At act 501, a set of intensity values associated with the feature vector is obtained from the region of interest in the medical image. The intensity values may be obtained from the pixels of the medical image. At act 502, the intensity values are distributed into a series of equally spaced intervals, wherein the first interval corresponds to minimum intensity value of a pixel and the last interval corresponds to maximum intensity value of a pixel. The normalization eliminates the impact of the scale factor associated with variable input dose. The calculated histogram effectively bins intensities according to the percentile variation (which has a fixed range) and not value variation. Therefore, if a patient had two medical images, one obtained with twice the injected dose of the radiopharmaceutical compound than the second medical image, the un-normalized histogram may contain maximum-intensity pixel(s) in two different bins. However, the normalized histogram the maximum-intensity pixels from both the medical images may occupy the same bin and are therefore comparable. The method acts of normalizing the feature vector may change based on the type of feature vector. The method acts of normalization of such feature vectors may be well-known to a person skilled in the art.

Figure 4:
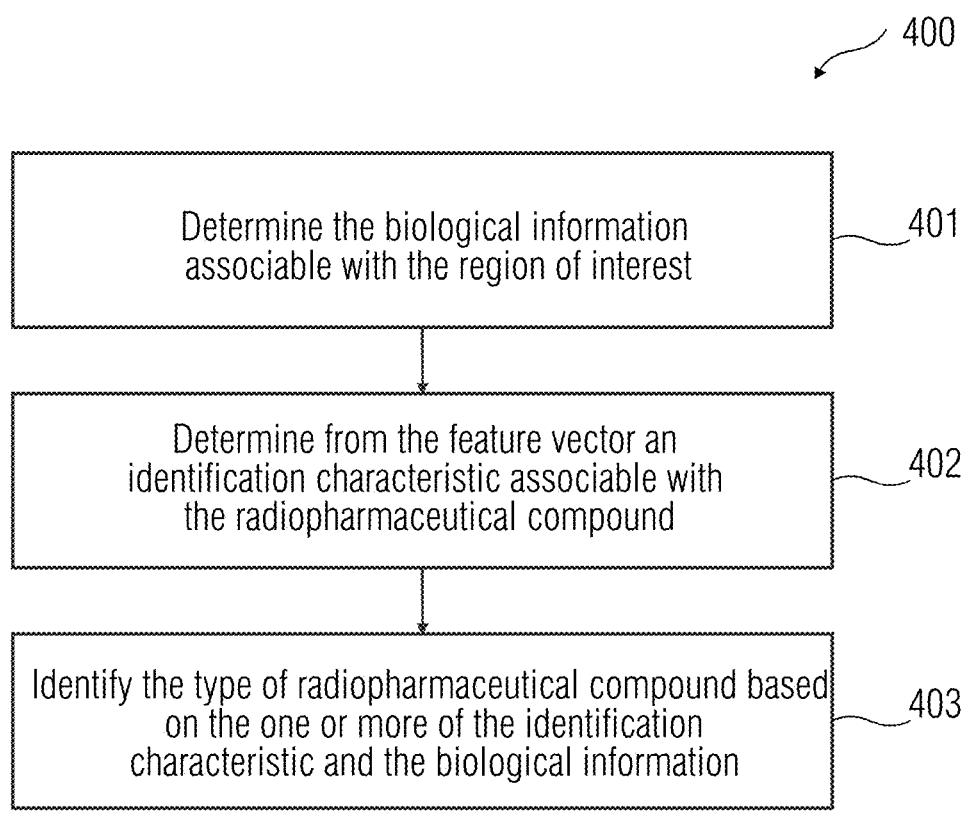
FIG. 4 illustrates a flowchart of an embodiment of a method of determining the radiopharmaceutical compound from the region of interest in the medical image.

At act 205 of the method 200, the radiopharmaceutical compound uptake is detected in the one or more regions of interest. The uptake of the radiopharmaceutical compound may be detected based on the intensity of the pixels in the medical image. At act 206, a type of the radiopharmaceutical compound is identified based on the feature vector and a biological information associated with the region of interest. The biological information may be, for example, but not limited to, a location of the region of interest known to bind to the radiopharmaceutical compound. The location of the region of interest may be an identified sub-region within the region of interest or an anatomically identified part of a patient habitus whose uptake of a radiopharmaceutical compound is markedly different in comparison to the other radiopharmaceutical compounds. In an embodiment, the location of the region of interest is a structural or anatomical region within an imaged organ. For example, there may be a plurality of radiopharmaceutical compounds that may bind to the brain during medical imaging. However, each of the plurality of the radiopharmaceutical compound may bind to a different location within the brain. Therefore, the location of the region of interest may vary based on the type of the radiopharmaceutical compound. Prior knowledge of the biological information such as the location of the region of interest enables accurate identification of the radiopharmaceutical compound used in the medical image. As illustrated in FIG. 6, different radiopharmaceutical compounds enhance different portions of the imaged organ or body part. Alternatively, the biological information may also be a distinguishing information drawn from a part of the patient habitus which provides. For example, so as to distinguish between FDG and amyloid tracers, the cortical shell of the brain may be analysed as a histogram of the cortical shell displays markedly different shapes for the two radiopharmaceutical compounds. FIG. 4 illustrates a flowchart of an embodiment of a method 400 of identifying a type of the radiopharmaceutical compound in the medical image. At act 401, an identification characteristic is determined from the feature vector. An identification characteristic may refer to a distinct attribute that may be identified from the feature vector. Such identification characteristic may also be derived from the biological information. The identification characteristic may be as a distinct mathematical prescription for a feature that encodes a known variation associated with a particular radiopharmaceutical compound for the region of interest. In an embodiment, if the feature vector is a histogram calculated based on the intensity of the medical image, the identification characteristic may be derived or identified from the histogram. For example, the identification characteristic may be a distinct peak in the histogram that may specific to a radiopharmaceutical compound.

Figure 8A:
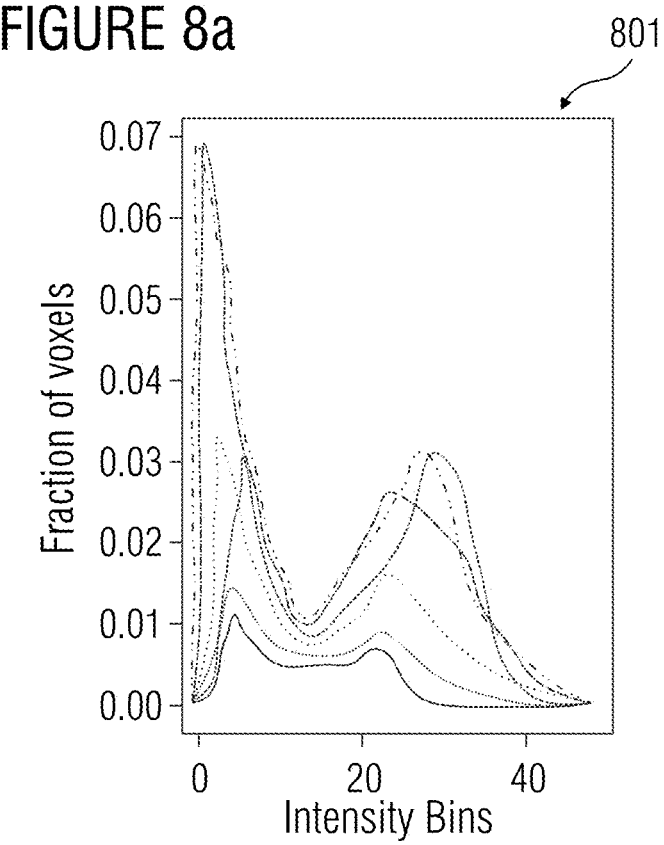
FIG. 8a illustrates an embodiment of a normalized feature vector associable with the radiopharmaceutical compound.
Figure 8B:
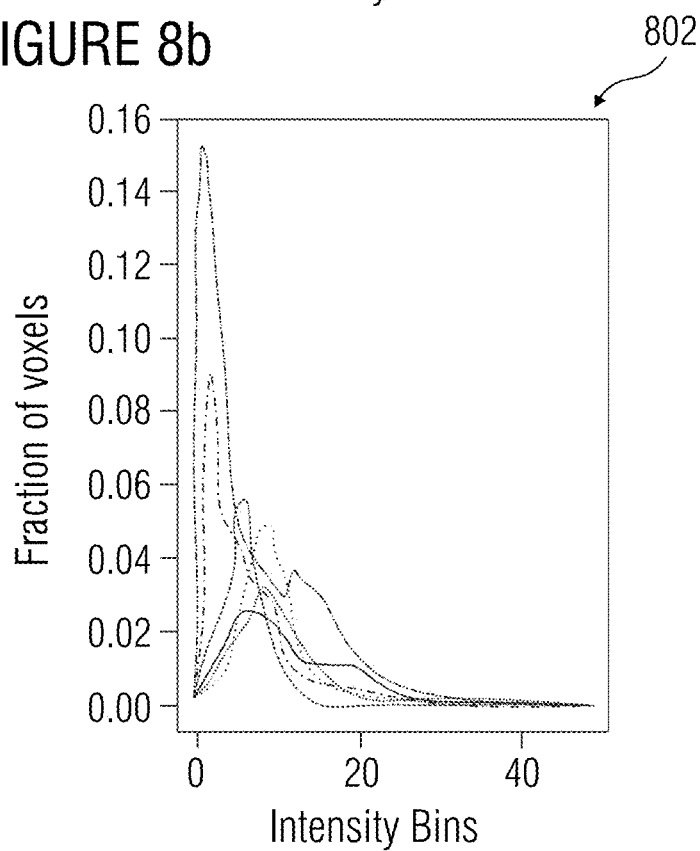
FIG. 8b illustrates another embodiment of a normalized feature vector associable with another radiopharmaceutical compound.

FIGS. 8*a* and 8*b* illustrate embodiments of normalized histograms 801, 802 of the cortical region 701, 702, and 703 depicted in FIG. 7. The histograms are obtained for the radiopharmaceutical compounds fluorodeoxyglucose (FDG) and florbetapir (AV45) respectively, with multiple datasets of intensity. The histogram for FDG shows a distinct second peak in FIG. 8*a*. The presence of this second peak may be used to distinguish FDG over other radiopharmaceutical compounds. FIG. 8*c* illustrates an averaged histogram 803 for FDG and AV45. The figure illustrates a presence of a distinct second peak for FDG over AV45 which enables FDG to be differentiated over AV45. The second peak generated for FDG may be the identification characteristic associable with the radiopharmaceutical compound. At act 402, the biological information associated with the region of interest is determined. In an embodiment, the identification characteristic may not be identified distinctly based on the feature vector. For example, for radiopharmaceutical compounds associated with amyloids, there may be only a single peak generated in the histogram. Thus, the identification of the radiopharmaceutical compound may be difficult based on such feature vectors. Therefore, the biological information associated with the region of interest, along with the identification characteristic may enable identification of the radiopharmaceutical compound used in the medical image.

Figure 9:
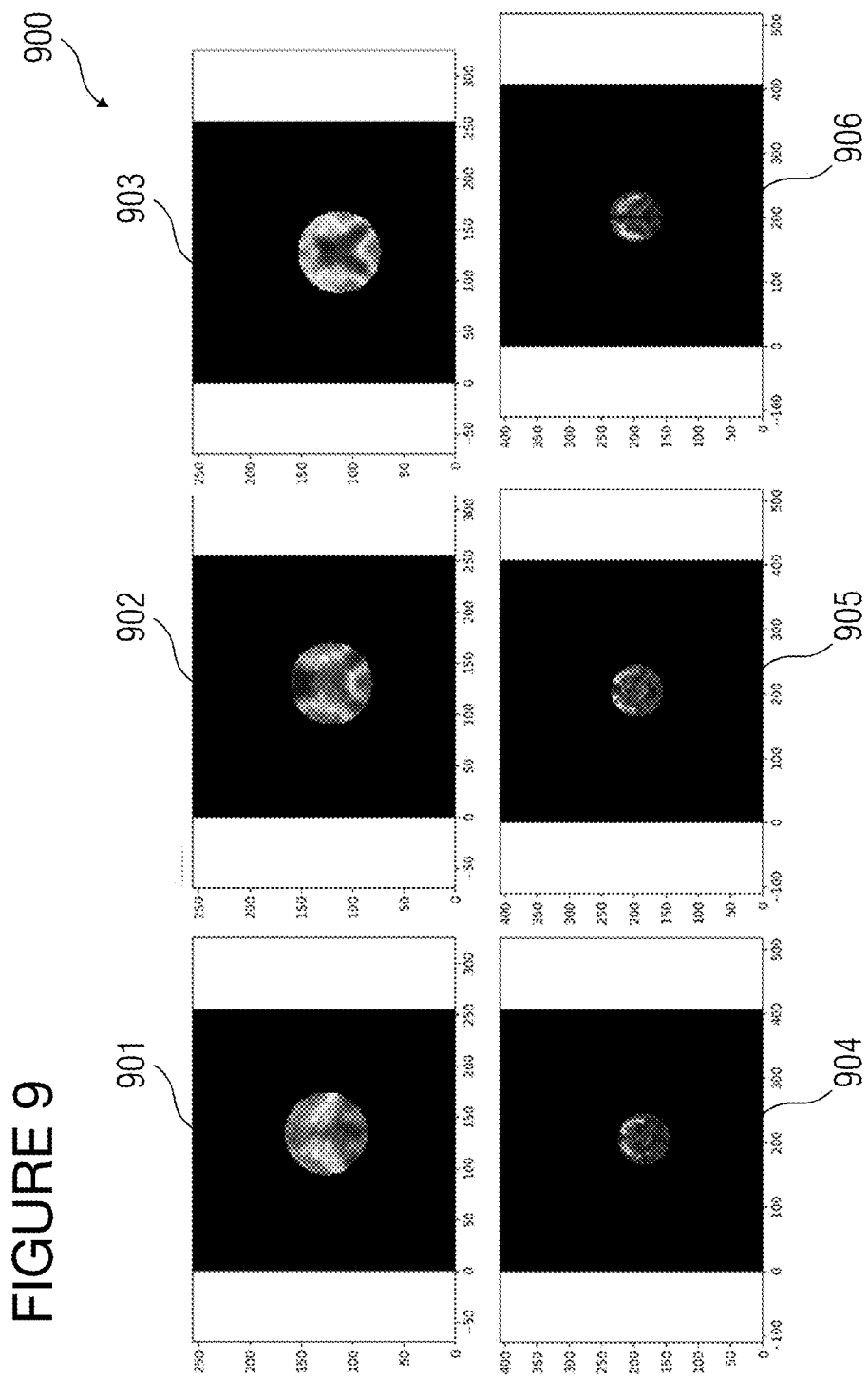
FIG. 9 illustrates an embodiment of a set of medical images depicting portions of the medical images where the radiopharmaceutical compounds are bound.

A radiopharmaceutical compound may be known to bind to a specific location within a region in a human body. FIG. 9 illustrates an embodiment of a set of medical images 900 depicting varying locations of the medical image where radiopharmaceutical compounds are bound within a region of interest. The medical images 900 illustrate a central region of basal ganglia bound with different radiopharmaceutical compounds. The medical images 901, 902, and 903 illustrate the basal ganglia region identified using AV45 and the medical images 904, 905, and 906 illustrate the basal ganglia region identified using another radiopharmaceutical compound, fluorodopa (FDOPA). FDOPA binds to a specific location within the basal ganglia in comparison to the AV45 whose uptake is more dispersed and non-specific. FDOPA specifically binds to dopamine receptors and enhances lobes of the basal ganglia. In an embodiment, the radiopharmaceutical compound may be identified based on the location of the region of interest where the presence of the radiopharmaceutical compound is determined. The medical image set 900 accurately captures the differing spatial uptake patterns in the basal ganglia between the two radiopharmaceutical compounds. The region of interest may be segmented out of the medical image. In an embodiment, if the region of interest is the basal ganglia, the segmentation may be performed geometrically such that a range of 20-40 millimetre region is defined in a medical image within 40% to 60% of the skull extremities. Using a fraction of the skull extent to define the region of interest is an embodiment of spatial scale invariant image processing, discussed earlier.

A classifier may be developed using machine learning techniques such as, but not limited to, linear/logistic regression, principal component analysis, generalized linear mixed models, random decision forests, support vector machines, and/or artificial neural networks. Literature for any known association of the radiopharmaceutical compound uptake with biological information, such as anatomical or structural regions may be used as input data to construct the classifier. The association of such anatomical or structural region with the radiopharmaceutical compound provides prior information to the classifier so as to localize differentiating image information in specific regions. This enables an increase in the signal to noise accuracy of the classifier, thereby eliminating the need for a large training data set that may not be available always. The classifier is trained using input data associated with normalized feature vectors that may uniquely enable identification of radiopharmaceutical compound from the medical image. The segmented regions of the medical image may be used as feature images to the machine learning classifier. Based on the feature images, the classifier may learn the differences and provide accurate classification of radiopharmaceutical compounds. The identification module 108 may be further configured to execute the classifier to determine the radiopharmaceutical compound.

In an embodiment, the classifier may be a support vector machine classifier (SVM). The support vector machine classifier has a single hyper-parameter. A hyper-parameter is a parameter whose value is set before the learning process begins. The value of the hyper-parameter may be determined from the training data. In an embodiment, in order that the selection of the hyper-parameter is not biased on a particular subset of training data, hundred random partitions of the input data may be constructed including equally sized training and testing subsets. The hyper-parameter may be varied over a range of values extending from $10^{-2}$ to $10^2$, equally spaced logarithmically. For each of the hundred partitions, SVM fitting coefficients are calculated for each value of the hyper-parameter based on the training data and the classification error is evaluated on the corresponding testing data. The averaged error over hundred partitions, for each value of the hyper-parameter, may provide a metric to decide what value of the hyper-parameter leads to the lowest classification error on unseen data. This value may be an optimal value of the hyper-parameter. The SVM fitting coefficients are determined by setting the value of the hyper-parameter to the optimal value.

EXPERIMENTAL RESULTS

In an embodiment, the optimal value of the hyper-parameter was set as 56.23. The classification accuracies for three different scenarios of FDG versus non-FDG classification were:

| Radiopharmaceutical compound | Predicted as FDG | Predicted as FDOPA |
| --- | --- | --- |
| FDG | 99.58% | 0.42% |
| FDOPA | 3.45% | 96.55% |

| Radiopharmaceutical compound | Predicted as FDG | Predicted as AV45 |
| --- | --- | --- |
| FDG | 99.4% | 0.6% |
| AV45 | 17.7% | 82.3% |

| Radiopharmaceutical compound | Predicted as FDG | Predicted as AV45 or FDOPA |
| --- | --- | --- |
| FDG | 94.18% | 5.82% |
| AV45 or FDOPA | 0.87% | 99.13% |

In all three scenarios, FDG is constantly detected with a sensitivity of 95% or higher due to the identification characteristic, e.g., the distinct peak identified from the histogram. The sensitivity of FDOPA is also high at 97%. The lower number obtained for AV45, e.g., 82% may be due to a lower number of training data set in comparison to FDG and FDOPA, which may have led to a possible bias in the classifier.

In an embodiment, the classifier may also be configured to provide an estimate of confidence of the prediction of the type of the radiopharmaceutical compound. Training data may possess anomalies or outliers which fall towards the boundary of the classifier's decision function. The confidence values for such outliers may be low (e.g., <0.5) whereas confident predictions have a confidence score of ~1.0. Therefore, the classifier may use a confidence score such that the type of the radiopharmaceutical compound will be identified only if the associated confidence score exceeds a threshold value. In another embodiment, if the classifier is unable to determine the radiopharmaceutical compound with confidence, the user may be prompted to predict and input the type of radiopharmaceutical compound.

In order to evaluate a patient's medical condition, the medical data including medical images of the patient may have to be compared with a medical database containing medical information related to normal individuals. Such medical data related to the patient may have to be registered with a reference template which may be specific to a type of radiopharmaceutical compound used for medical imaging. Therefore, prior knowledge of the type of radiopharmaceutical compound used in the medical imaging is important. The method and system provide for an automatic identification of the type of the radiopharmaceutical compound, thereby enabling faster registration of the patient's medical information with the reference template. Thus, the registered result is made available to a physician faster, reducing the time taken for medical analysis. Radiopharmaceutical compounds used in molecular imaging are associated with specific physiological functions and bind to well-defined and known anatomical regions in the body. This biological information is harnessed to enable efficient, accurate and faster determination of radiopharmaceutical compounds in medical images. While conventional data-drive methods seek to learn this information indirectly from a vast cohort of training and testing data, a method that translates the biological information into useful and relevant feature information a priori may enable a more accurate and efficient method of determining radiopharmaceutical compounds that requires a smaller number of training and testing datasets for constructing a model.

The foregoing examples have been provided merely for the purpose of explanation and are in no way to be construed as limiting of the present disclosure. While the disclosure has been described with reference to various embodiments, it is understood that the words, which have been used herein, are words of description and illustration, rather than words of limitation. Further, although the disclosure has been described herein with reference to particular means, materials, and embodiments, the disclosure is not intended to be limited to the particulars disclosed herein; rather, the disclosure extends to all functionally equivalent structures, methods and uses, such as are within the scope of the appended claims. Those skilled in the art, having the benefit of the teachings of this specification, may affect numerous modifications thereto and changes may be made without departing from the scope and spirit of the disclosure in its aspects.

The invention claimed is:

1. A method of determining a radiopharmaceutical compound used in a medical image, the method comprising:
    obtaining the medical image from a source through an interface;
    identifying a region of interest in the medical image;
    generating a feature vector associable with the region of interest;
    detecting an uptake of the radiopharmaceutical compound in the region of interest; and
    identifying a type of the radiopharmaceutical compound based on the feature vector and a biological information associated with the region of interest,
    wherein the identifying of the type of the radiopharmaceutical compound is based on the uptake of the radiopharmaceutical compound within an anatomical region being markedly different in comparison to other radiopharmaceutical compounds in the anatomical region.

2. The method of claim 1, wherein the identifying of the region of interest comprises determining a region in the medical image exhibiting presence of the radiopharmaceutical compound based on the biological information.

3. The method of claim 1, wherein the biological information comprises one or more of an anatomical region and a known variation associated with the radiopharmaceutical compound for the region of interest.

4. The method of claim 1, wherein in the identifying of the type of the radiopharmaceutical compound, the method further comprises:
    determining the biological information associable with the region of interest;

determining from the feature vector an identification characteristic associable with the radiopharmaceutical compound; and identifying the type of the radiopharmaceutical compound based on the one or more of the identification characteristic and the biological information.

5. The method of claim 1, further comprising:

normalizing the feature vector to be spatial-scale and intensity independent.

6. The method of claim 1, wherein a location of the region of interest corresponds to a location of a structural or anatomical region within an imaged organ.

7. The method of claim 1, wherein the medical image is a positron-emission tomography image or a single-photon emission computed tomography image.

8. A system for determining a radiopharmaceutical compound in a medical image, the system comprising:

a processing unit;

a medical database coupled to the processing unit;

a memory coupled to the processing unit, the memory comprising an identification module configured to:

obtain the medical image from a source through an interface;

identify a region of interest in the medical image;

generate a feature vector associable with the region of interest;

detect an uptake of the radiopharmaceutical compound in the region of interest; and identify a type of the radiopharmaceutical compound based on the feature vector and a biological information associated with the region of interest, wherein the identifying of the type of the radiopharmaceutical compound is based on the uptake of the radiopharmaceutical compound within an anatomical region being markedly different in comparison to other radiopharmaceutical compounds in the anatomical region.

9. The system of claim 8, wherein in the identifying of the region of interest, the identification module is configured to determine a region in the medical image exhibiting a presence of the radiopharmaceutical compound based on the biological information.

10. The system of claim 8, wherein in the identifying the type of the radiopharmaceutical compound, the identification module is further configured to:

determine the biological information associable with the region of interest;

determine from the feature vector an identification characteristic associable with the radiopharmaceutical compound; and identify the type of radiopharmaceutical compound based on the one or more of the identification characteristic and the biological information.

11. The system of claim 8, wherein the identification module is further configured to normalize the feature vector to be spatial-scale and intensity independent.

12. The system of claim 8, wherein a location of the region of interest corresponds to a location of a structural or anatomical region within an imaged organ.

13. The system of claim 8, wherein the medical image is a positron-emission tomography image, a computed tomography image, or a magnetic resonance imaging image.

14. A non-transitory computer-readable storage medium having machine-readable instructions stored therein, that when executed by a server, cause the server to:

obtain a medical image from a source through an interface;

identify a region of interest in the medical image;

generate a feature vector associable with the region of interest;

detect an uptake of a radiopharmaceutical compound in the region of interest; and identify a type of the radiopharmaceutical compound based on the feature vector and a biological information associated with the region of interest, wherein the identifying of the type of the radiopharmaceutical compound is based on the uptake of the radiopharmaceutical compound within an anatomical region being markedly different in comparison to other radiopharmaceutical compounds in the anatomical region.

15. The storage medium of claim 14, wherein, in the identification of the type of the radiopharmaceutical compound, the instructions cause the server to:

determine the biological information associable with the region of interest;

determine from the feature vector an identification characteristic associable with the radiopharmaceutical compound; and identify the type of the radiopharmaceutical compound based on the one or more of the identification characteristic and the biological information.

16. The storage medium of claim 14, wherein the instructions further cause the server to:

normalize the feature vector to be spatial-scale and intensity independent.

17. The storage medium of claim 16, wherein a location of the region of interest corresponds to a location of a structural or anatomical region within an imaged organ.

* * * * *